(12) United States Patent
Fermier et al.

(10) Patent No.: US 6,743,356 B1
(45) Date of Patent: Jun. 1, 2004

(54) HIGH THROUGHPUT HIGH PERFORMANCE CHROMATOGRAPHY SYSTEM

(75) Inventors: Adam M. Fermier, Easton, PA (US); Elias H. Hochman, deceased, late of Doylestown, PA (US), by Jill N. Jones, executor; Norberto A. Guzman, East Brunswick, NJ (US); Stephen Scypinski, Basking Ridge, NJ (US)

(73) Assignee: Johnson & Johnson, New Brunswick, NJ (US)

( * ) Notice: Subject to any disclaimer, the term of this patent is extended or adjusted under 35 U.S.C. 154(b) by 0 days.

(21) Appl. No.: 09/699,212

(22) Filed: Oct. 27, 2000

(51) Int. Cl.$^7$ ................................................. B01D 15/08
(52) U.S. Cl. .................... 210/198.2; 210/656; 210/659; 210/143
(58) Field of Search ................. 210/635, 656, 210/659, 101, 143, 198.2; 95/82, 86; 96/101, 104

(56) References Cited

U.S. PATENT DOCUMENTS

| | | | | |
|---|---|---|---|---|
| 3,398,689 A | * | 8/1968 | Allington | 210/198.2 |
| 4,045,343 A | * | 8/1977 | Achener | 210/198.2 |
| 4,128,476 A | * | 12/1978 | Rock | 210/198.2 |
| 4,310,420 A | * | 1/1982 | Konishi | 210/198.2 |
| 4,311,586 A | * | 1/1982 | Baldwin | 210/198.2 |
| 4,422,942 A | * | 12/1983 | Allington | 210/659 |
| 4,478,713 A | * | 10/1984 | Girot | 210/198.2 |
| 4,595,495 A | * | 6/1986 | Yotam | 210/198.2 |
| 4,595,496 A | * | 6/1986 | Carson | 210/198.2 |
| 4,669,502 A | | 6/1987 | Lonardi et al. | 137/624.18 |
| 4,728,434 A | * | 3/1988 | Trafford | 210/656 |
| 4,834,534 A | * | 5/1989 | Wiget | 356/410 |
| 4,840,730 A | * | 6/1989 | Saxena | 210/198.2 |
| 4,879,029 A | * | 11/1989 | Whitehead | 210/198.2 |
| 4,889,148 A | * | 12/1989 | Smazik | 251/129.07 |
| 5,057,216 A | * | 10/1991 | Chervet | 210/198.2 |
| 5,374,029 A | * | 12/1994 | Bailey | 251/129.16 |
| 5,654,201 A | * | 8/1997 | Capuano | 436/124 |
| 5,800,784 A | | 9/1998 | Horn | 422/101 |
| 5,852,231 A | * | 12/1998 | Kaji | 210/198.2 |
| 6,019,897 A | * | 2/2000 | Horsman | 210/198.2 |
| 6,027,873 A | | 2/2000 | Schellenberger et al. | 435/4 |
| 6,080,318 A | * | 6/2000 | Gumm | 210/198.2 |
| 6,197,198 B1 | * | 3/2001 | Messinger | 210/198.2 |
| 6,210,571 B1 | * | 4/2001 | Zambias | 210/198.2 |
| 6,318,157 B1 | * | 11/2001 | Corso | 210/198.2 |
| 6,355,163 B2 | * | 3/2002 | Hindsgaul | 210/198.2 |
| 6,358,413 B1 | * | 3/2002 | Maiefski | 210/198.2 |
| 6,372,142 B1 | * | 4/2002 | Gjerde | 210/635 |

OTHER PUBLICATIONS

Snyder, Introduction to Modern Liquid Chromatography, John Wiley, 1979, pp. 105–106.*

(List continued on next page.)

Primary Examiner—Ernest G. Therkorn
(74) Attorney, Agent, or Firm—Darby & Darby (57) ABSTRACT

A high throughput high performance chromatography system operating at a high mixing pressure including a plurality of pressurized solvent reservoirs, e.g. pumps, each maintaining an associated solvent at a substantially constant pressure. A plurality of flow control valves are connected downstream or upstream of the reservoirs for controlling the flow rate of the solvent into the respective columns. The number of reservoirs equals the number of solvents. Accordingly, the system reduces the number of pumps required thereby saving money and space. Furthermore, the system increases sample throughput, accelerates method development and minimizes organic waste.

23 Claims, 7 Drawing Sheets

OTHER PUBLICATIONS

Korfmacher, Walter A., et al., *Demonstration of the Capabilities of a Parallel High Performance Liquid Chromatography Tandem Mass Spectrometry System for Use in the Analysis of Drug Discovery Plasma Samples, Rapid Communications in Mass Spectrometry*, vol. 13, pp. 1991–1998 (1999).

Wang, T., et al., *A Multiple Electrospray Interface for Parallel Mass Spectrometric Analyses of Compound Libraries, Combinatorial Chemistry & High Throughput Screening*, vol. 2, pp. 327–334 (1999).

He, Bing, et al., *Fabrication of Nanocolumns for Liquid Chromatography, Anal. Chem.*, vol. 70, pp. 3790–3797 (1998).

Weller, Harold N., et al., *High throughput analysis and purification in support of automated parallel synthesis, Molecular Diversity* vol. 3, pp. 61–70 (1997).

Woodbury Jr., et al., *Sample Multiplexing for Greater Throughput in HPLC and Related Methods, Anal. Chem.*, vol. 67, pp. 885–890 (1995).

Isobe, Toshiaki, et al., *Automated two–dimensional liquid chromatogaphic system for mapping proteins in highly complex mixtures, Journal of Chromatography*, vol. 588, pp. 115–123 (1991).

Chin, Wilkin, Krohne America, Inc., *SENSORS*, Oct. 1994, pp: 55, 56 & 58.

Huang, Xiaohua C., et al., 1992, *Anal. Chem.*, 64, 967–972.

Vickrey, Thomas M., *Chromatographic Science Series*, vol. 23, pp:42–45, 1983.

Skoog, Douglas A., et al., *Principles of Instrumental Analysis*, $5^{th}$ Edition, pp: 725–743, 1998.

Kiplinger, Jeffrey P., et al., 1998, *Rapid Commun. Mass Spectrom.*, 12, 658–664.

Brooks QUANTIM Precision Mass Multivariable Flow Measurement and Control, *Design Specifications, DS–Qm*, Jul., 1999.

* cited by examiner

HIGH THROUGHPUT HIGH PERFORMANCE CHROMATOGRAPHY SYSTEM

FIELD OF THE INVENTION

The present invention relates to a chromatography system, and in particular to a high throughput analytical chromatography system and method for operating the same to increase sample throughput and method development.

DESCRIPTION OF RELATED ART

Separation science is a universal technique that benefits most scientists. Chromatographic separations provide a means to determine to what extent a reaction has yielded the desired products, to monitor impurities and dissolution profiles, and to study degradation pathways in drug products. Disadvantageously, chromatographic separations are relatively long and tedious processes with analysis times up to approximately 1 hour. Another problem associated with conventional chromatographic separations is the method development time. Screening multiple columns, materials and instruments to achieve optimum separation is labor intensive.

Heretofore, conventional analytical HPLC separation devices consist of a flow-metering pump to control volumetric flow rates of solvent gradients. Either low or high pressure mixing is used to produce the gradient. As the names imply, low pressure and high pressure mixing refer to the forming of the gradient either pre- or post-pump, respectively. To increase the capacity of the system it would be desirable to build an instrument capable of running several columns in parallel. For example, for parallel processing of 8 columns, 8 conventional detectors would be required and, depending on how the gradient is formed, either 8 or 16 pumps would be required for low pressure and high pressure mixing, respectively. The increased number of pumps and detectors necessary for this set up is costly and would take up a significant amount of space.

It is therefore desirable to develop a parallel processing chomatographic separation system that would be more cost effective, take up less space and be convenient and easy to use by the operator. As a result, the sample throughput time would increase as the method development time decreases.

SUMMARY OF THE INVENTION

For the purposes of the present invention the generic term high throughput high performance chromatography (HT-HPC) is defined to include high throughput high performance liquid, gas, capillary, microbore, preparative, electro, and supercritical fluid chromatography systems.

The present invention is directed to a HT-HPC system and method that solves the aforementioned problems and disadvantages associated with conventional serial systems and techniques.

The present invention is directed to a HT-HPC system that provides independent control of flow rates into an array of columns via flow control valves. Flow control valves are a convenient means to run multiple separations simultaneously, i.e., parallel processing, from common pressurized solvent reservoirs. The valves allow a manifold of columns to be analyzed in a high pressure mixing mode. The high pressure mixing mode advantageously lowers gradient dwell time and subsequently allows faster equilibration and analyses times.

In accordance with the present invention, the HT-HPC system and technique is more efficient in that it requires less analysis and method development time due to its parallel configuration. Accordingly, the system and method in accordance with the invention can produce results in a shorter period of time because multiple samples can be run in the same period of time as a single sample using a conventional system.

Another advantage of the present invention HT-HPC system is the design of high pressure mixing for relatively low gradient dwell times.

The present invention is directed to a high throughput high performance chromatography system operating at a high mixing pressure including a plurality of pressurized solvent reservoirs, e.g., pumps, each maintaining an associated solvent at a substantially constant pressure. A plurality of flow control valves are connected downstream of the pressurized solvent reservoirs for controlling the flow rate of the solvent into each column. The number of pressurized solvent reservoirs equals the number of solvents. Accordingly, the system reduces the number of pressure solvent reservoirs required thereby saving money and space. Furthermore, the system increases sample throughput, accelerates method development and minimizes organic waste. In an alternative embodiment, instead of each valve being associated with a single column, a plurality of columns may be connected downstream of each valve to form an array, whereby the valves associated with a particular lane control the flow rate of the solvent into the columns associated with that lane. This adds another dimension to the separation capabilities of the instrument thereby providing a very flexible instrument for method development and sample throughput. Additional dimensions may be added to the system, as desired.

Another embodiment in accordance with the present invention provides a s-shaped sample detection cell for measuring absorbance of the sample. The cell includes a section of tubing connected to the flow stream via two tees. Fiber optics deliver the light to the cell and directs the transmitted light from the cell to the detector. A single detector may be used for all parallel processed channels thereby reducing the cost and saving space.

Still another embodiment discloses a method for using the high throughput high performance chromatography system described above. One or more solvents are maintained at a substantially constant pressure using an associated pressurized solvent reservoir. The flow rate of the solvent into respective columns is controlled using a flow control valve connected downstream of each pressurized solvent reservoir. The gradient of each column may be independently adjusted.

BRIEF DESCRIPTION OF THE DRAWINGS

The foregoing and other features of the present invention will be more readily apparent from the following detailed description and drawings of illustrative embodiments of the invention wherein like reference numbers refer to similar elements throughout the several views and in which.

DETAILED DESCRIPTION OF THE INVENTION

Figure 1A:
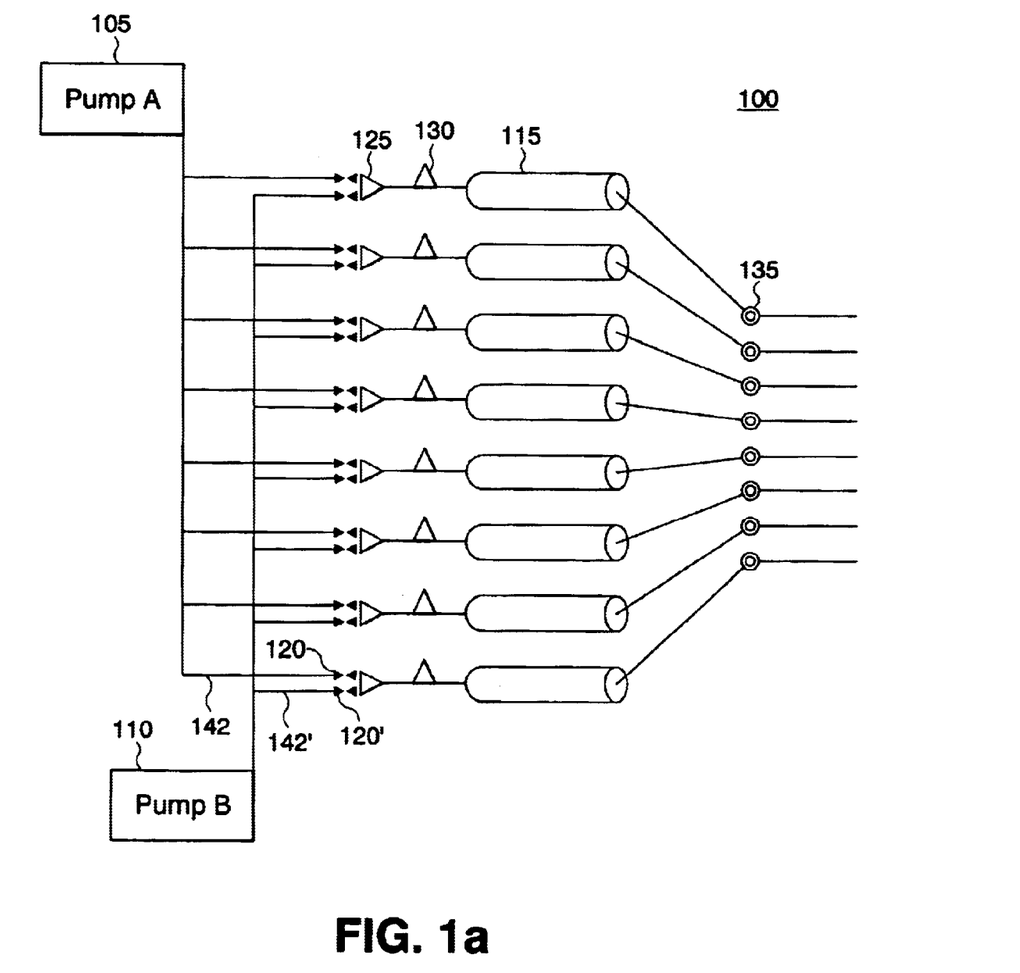
FIG. 1a is an exemplary 8 channel High Throughput High Performance Chromatography system in accordance with the present invention employing a gradient elution.

FIG. 1a is an exemplary High Throughput High Performance Chromatography (HT-HPC) system 100 in accordance with the present invention using flow control valves rather than pumps for regulating the flow into each column. HT-HPC system 100 includes two pressurized solvent reservoirs 105, 110 delivering solvents A and B, respectively, at a substantially constant pressure to all 8 columns 115 through a manifold. Pressurized solvent reservoirs 105, 110 may be any conventional pump that is able to generate a head pressure, such as a syringe pump or a reciprocity pump. Alternatively, any device may be used that is able to provide a substantially constant pressure solvent source, such as an accumulator piston. Although the present invention is shown and described with respect to a chromatographic device having 8 columns and two solvents A, B, it is within the intended scope of the present invention to use the device with any number of desired columns and/or solvents.

Since the configuration with respect to each column is the same, the arrangement associated with only the first column 115 will be described in detail. Pressurized solvent reservoirs 105, 110 are connected to column 115 by tubing 142, 142'. Unlike conventional HT-HPC devices in which the flow rate of the solvents into the columns is adjusted by pumps, the HT-HPC system in accordance with the present invention employs respective automated flow control valves 120, 120' to adjust the flow rate of solvents A, B, into the column 115. In a preferred embodiment, metering valves are capable of controlling the flow below mL per minute, such as the QUANTIM Mass Flow Meter manufactured by Brooks Instrument, Inc., are used. Flow control valves 120, 120' comprise three basic components: a flow meter, a valve, and software/hardware to operate the valve. Conventional flow meters are turbine- temperature-, pressure- and mass-based flow meters. Integrated flow meters and valves are commercially available as flow control valves. These integrated flow control valves are relatively expensive. Alternatively, a less expensive high-pressure solenoid controlled using pulse width modulation, software and a flow meter capable of metering the desired flow range may be used. The use of valves instead of pumps, as in conventional HT-HPC systems, is beneficial in several respects. A substantially constant flow and pulseless rate may be realized by using a valve, which is otherwise impractical when using a pump. Because the valve produces a substantially constant flow source, precise or refined control over the flow rate is possible with less waste. Furthermore, the use of valves to control the flow rate allows the solvent streams to be split off and mixed independently together to produce a user defined gradient for each lane from one or more common pressurized solvent reservoirs.

A high pressure mixing tee or gradient mixing chamber 125 connects the outputs from the automated flow metering valves 120, 120' and mixes together the two solvents A and B prior to entering the column 115. Disposed between the mixing tee 125 and column 115 is an injector 130 for introducing the sample into the column 115. Downstream of column 115 is a sample detection cell 135, for example, an ultraviolet detector, for detecting the absorbance data from each column.

Figure 1B:
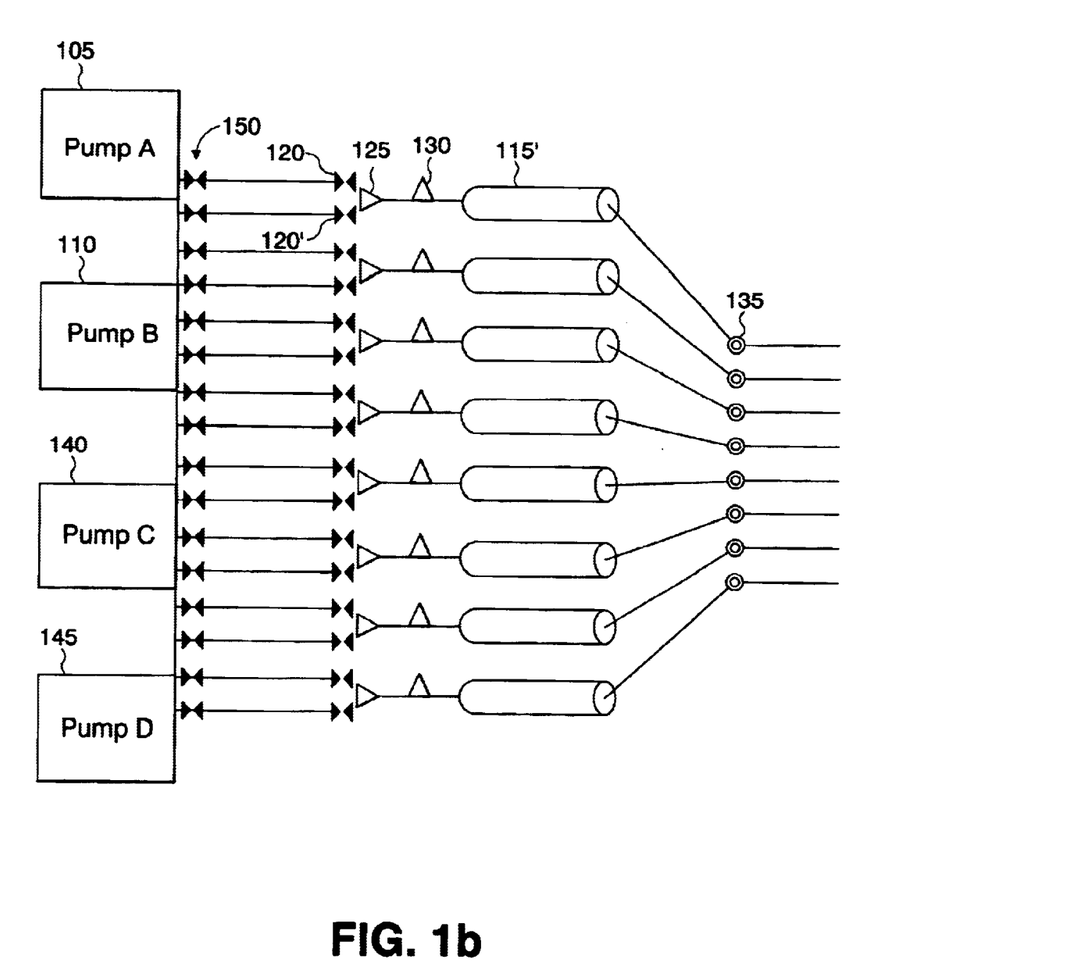
FIG. 1b is an exemplary 8×8 High Throughput High Performance Chromatography array in accordance with the present invention.

The 8 channel parallel processing HT-HPC instrument shown in FIG. 1a may be modified into an 8×8 array of HPC columns, as shown in FIG. 1b. The 8×8 array has four pressurized solvent reservoirs 105, 110, 140, 145 for solvents A, B, C, D, respectively. A solvent selection valve 150 is disposed in each lane. This array provides greater versatility in that more columns may be analyzed in the same run. Although an 8×8 array is shown in FIG. 1b, it is within the intended scope of the invention to configure an M×N array, where M and N≧1. Since only two flow control valves 120, 120' are provided for each lane, the gradient into each column may comprise at most two different solvents. Four flow control valves can be employed in each lane to produce a gradient that is a mixture of four or less solvents. Alternatively, as shown in FIG. 1c, the flow meter 127 and flow control valve 120 may be located at two different locations in the flow stream to minimize the number of flow meters and pressure specifications.

Figure 1C:
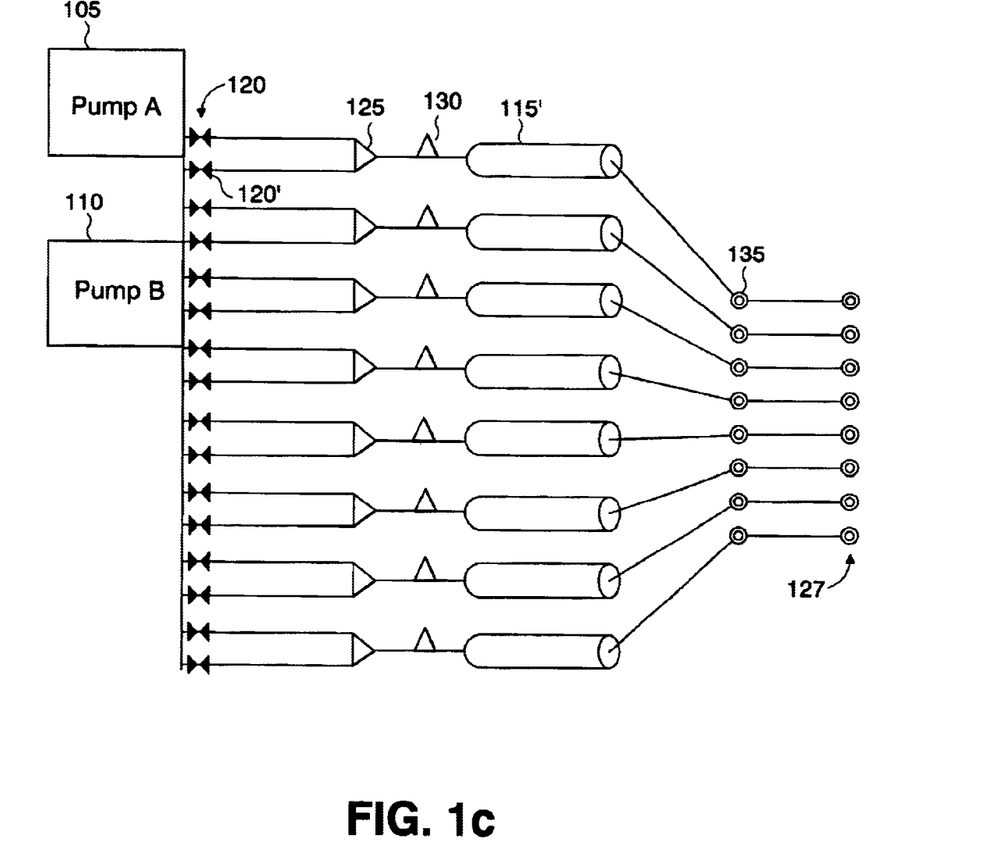
FIG. 1c is another exemplary 8×8 High Throughput High Performance Chromatography array in accordance with the present invention.
Figure 1D:
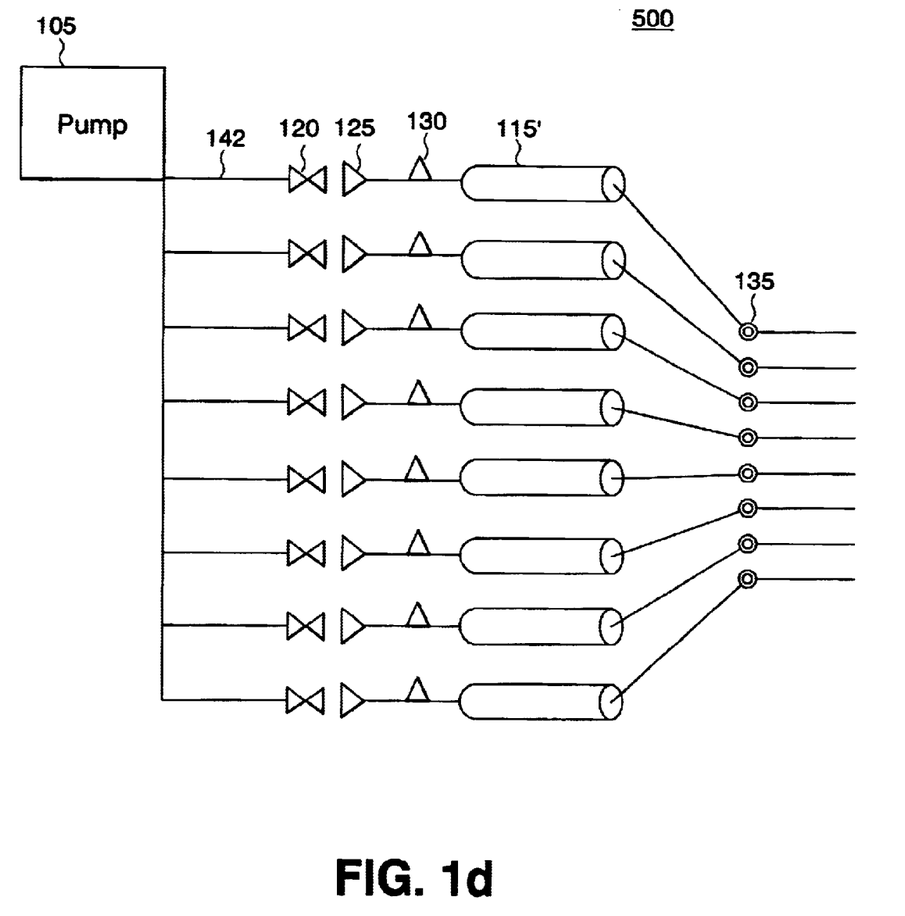
FIG. 1d is an exemplary isocratic setup of an 8 channel High Throughput High Performance Chromatography array in accordance with the present invention.

Although a separation system in accordance with the present invention has been shown in FIGS. 1a, 1b, and 1c for gradient elution wherein the two or more solvents form a gradient, it is within the intended scope of the invention to use the HT-HPC system for isocratic elution, that employs a single solvent of substantially constant composition. FIG. 1d is an exemplary 8 channel High Throughput High Performance Chromatography system 600 employing an isocratic elution. Since a single solvent of substantially constant composition is employed, only a single pressurized solvent reservoir 105 and one flow metering valve 120 for each lane is required.

Figure 2:
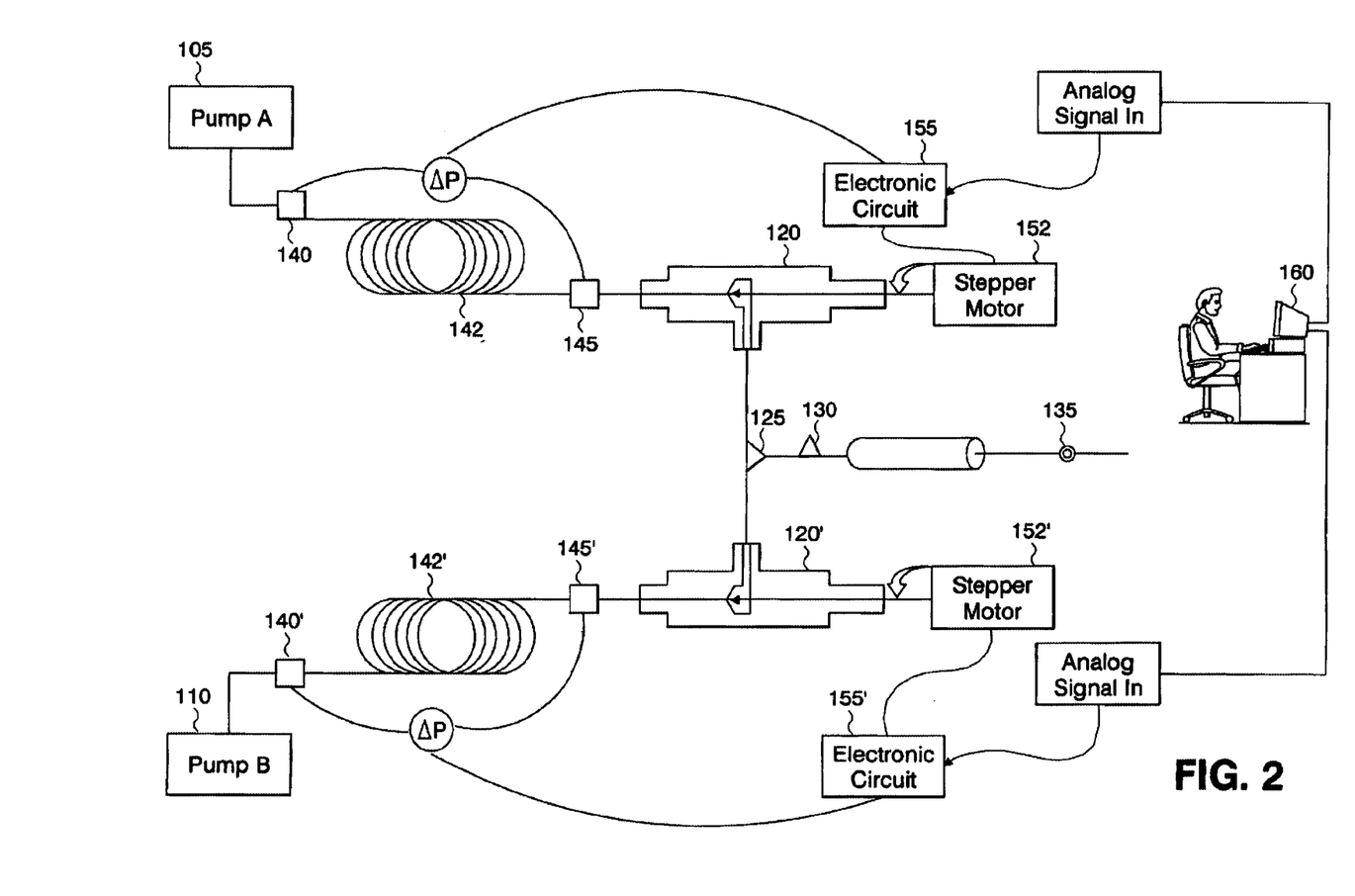
FIG. 2 is an exemplary flow metering system in FIGS. 1a–1d.

The flow rates of solvent into each column of FIGS. 1a, 1b, 1c, and 1d are controlled by flow control valves. As previously mentioned, flow control valves comprise of three basic components: a flow meter, a valve, and software/hardware to operate the valve. Conventional flow meters are turbine- temperature-, pressure- and mass-based flow meters. FIG. 2 is an exemplary flow control valve including a pressure based flow meter, stepper driven valve and a computer. The configuration shown in FIG. 2 is a single channel instrument. This configuration can be associated with column 115 in the column array in FIGS. 1a–1d. The same flow control valve arrangement is employed for each of the 8 columns in the array. Solvent from the pressurized solvent reservoirs 105, 110 flows through the tubing 142, 142' respectively, to the column 115. A first pair of pressure transducers 140, 145 and 140', 145' are disposed along the tubing 142, 142', respectively. Each pair of pressure transducers measures the respective pressure differential across a predetermined length of the tubing. The volumetric flow rate Q can be derived knowing the measured pressure drop using the Hagen-Poiseuille equation $$Q = \frac{\Delta P (dc)^4 \pi}{128 L \eta}$$

where

L is a predetermined length of tubing;

ΔP is the pressure differential or drop measured along the predetermined length of tubing;

dc is the diameter of the tubing; and

η is the viscosity of the solvent.

Since the pressure differential ΔP and flow rate Q are directly related, the flow rate Q can be indirectly measured using the proposed FMS. Therefore, the FMS indirectly measures or calculates the flow rate of the solvent into the column by monitoring the pressure differential ΔP across the tubing using two pressure transducers. The flow control valves 120, 120' are adjusted by motors 120, 120' to control the pressure differential ΔP and hence the flow rate Q of the solvents A, B. A closed loop system, as described here, will enable the ultimate control of the flow rates desired.

The user inputs at a computer 160 a desired gradient composition, e.g. 60:40 A:B, for each column in the array. The computer generates an analog signal that is transmitted to electrical circuits 155, 155', which control the motors 152, 152' so that the desired gradient composition input by the user at the computer matches the flow rate of the solvent based on the pressure differential as measured by the pressure transducers. If the pressure differential ΔP for the particular solvent is too high, hence the flow rate Q is too large, the stepper motor will start closing the associated valve until the targeted pressure differential ΔP is achieved. It is the intended scope of the present invention to employ any conventional flow meter and valve in the flow control metering valves.

The present inventive parallel processing chromatographic system is advantageous in that the user can independently specify gradients for each column. Thus, the user can define various gradients for one experiment and then on the following experiment reconfigure the system for sample throughout by making all the gradients the same. Alternatively, different stationary phases can be tested in each column during a single experiment, again speeding up the method development time. Parallel processing in accordance with the present invention is an effective method to decrease cycle times. Currently methods can take up to a month, this invention has the ability to reduce these times by a factor of 10.

Figure 3:
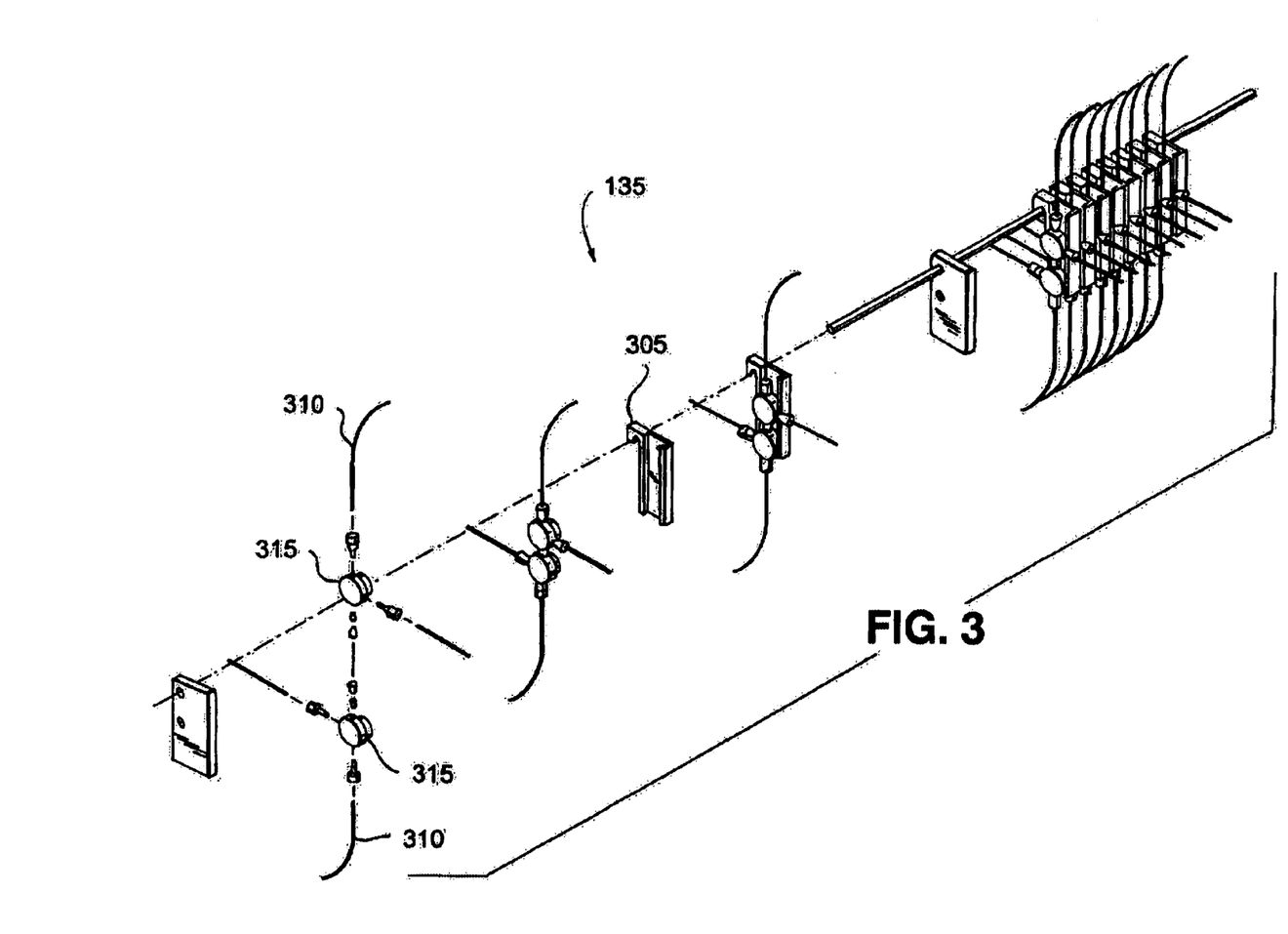
FIG. 3 is an isometric view of an exemplary sample detection flow cell in accordance with the present invention.

It is also desirable to develop a sample detection cell 135 with a longer path length compared to conventional detections systems. A longer path length enables lower detection limits. FIG. 3 is an isomeric view of the fiber optic sample detection cell 135 in FIGS. 1a, 1b, 1c, 1d. Sample detection cell 135 is supported in a mounting block 305, which is disposed between two tee connections 315. Fiber optics 310 deliver and collect the light from the sample detection cell 135. The s-shaped configuration of the sample detection cell 135 provides a longer flow path length and requires less space than conventional detection cells.

Figure 4:
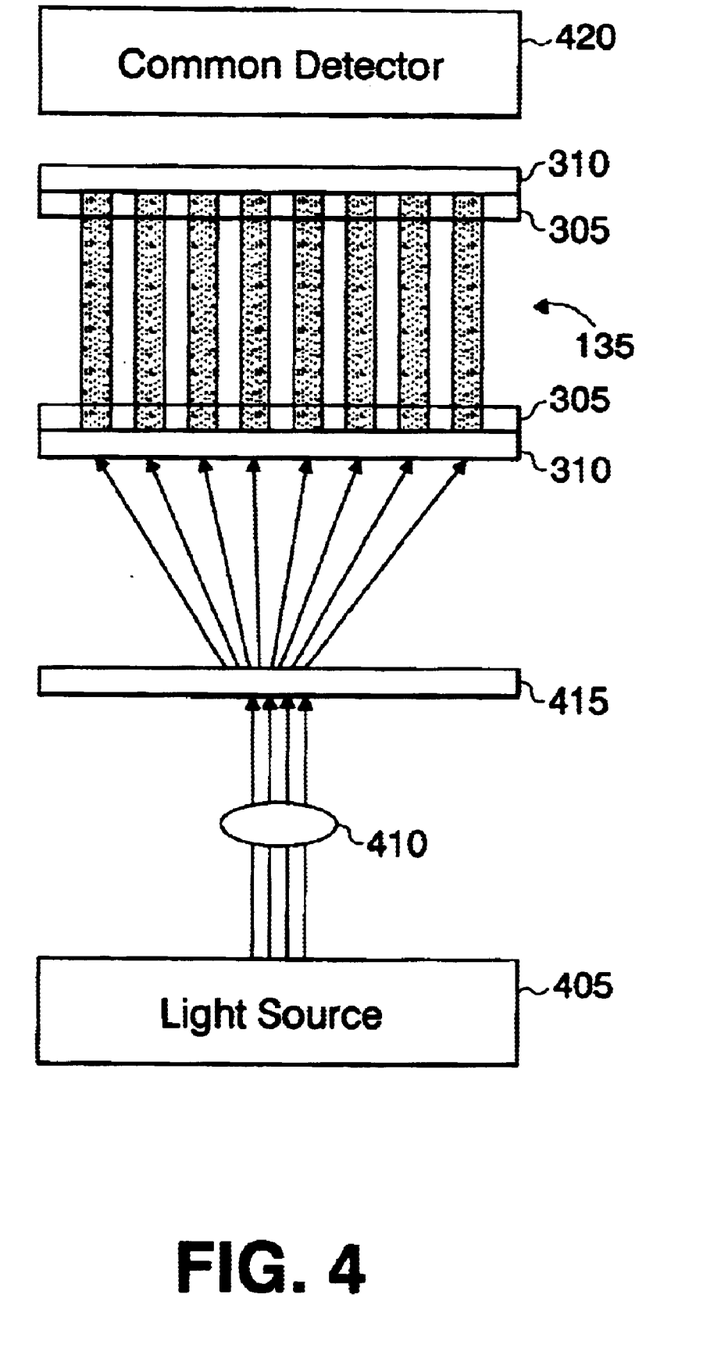
FIG. 4 is an exemplary detection system.

FIG. 4 diagrammatically depicts an exemplary detection system for the 8 column array in FIG. 1a. Light from a light source 405, such as a mercury arc lamp, is passed through a monochromater filter 410 to allow wavelength and bandwidth selection. The filtered light passes through a bundle of fiber optics to illuminate all of the sample detection cells 135. A common detector 420, such as a charge coupled device or photodiode array, collects the absorbance data from all 8 columns and produces 8 chromatograms.

The benefits of the system proposed here is that the gradients can be formed using two pressurized solvent reservoirs instead, as traditionally required for 8 separations, of using 16 pumps for high pressure mixing or 8 pumps for low pressure mixing. The design not only saves money by combining 8 instruments thereby saving cost and space, but also allows for faster method development time and sample throughput by generating 8 chromatograms at once. As mentioned earlier, this can be expected to reduce the sample throughput and methods development times by at least a factor of 10.

In summary, the proposed HT-HPC in accordance with the present invention increases sample throughput, accelerates method development, and minimizes organic waste. HP-HPC parallel processing in accordance with the present invention is also suitable for mobile phase optimization, pH optimization, column screening, sample throughput, and preparative chromatography.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps which perform substantially the same function, in substantially the same way, to achieve the same results are within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

What is claimed is:

1. A high throughput high performance chromatography system operating at a high mixing pressure, comprising:
    at least one pressurized solvent reservoir maintaining an associated solvent at a substantially constant pressure, wherein the number of solvent reservoirs equals the number of solvents;
    a plurality of flow control valves connected downstream of and in fluid communication with each of said reservoirs;
    a plurality of columns connected downstream of said at least one reservoir, said valves controlling the flow rate of the solvent into the respective columns; and
    a plurality of injectors in communication with said plurality of columns such that one injector introduces one sample into one column, the injectors being operable such that multiple samples can be simultaneously introduced into multiple columns and a sample gradient introduced to each column is controllable independent from gradients introduced to other columns.

2. The system in accordance with claim 1, further comprising an s-shaped sample detection cell for measuring absorbance.

3. The system in accordance with claim 1, wherein said solvent reservoir is selected from the group consisting of a pump and an accumulator piston.

4. The system in accordance with claim 1, wherein each flow control valve comprises a valve and a flow meter.

5. The system in accordance with claim 1, wherein each flow control valve comprises a high-pressure solenoid controlled using pulse width modulation and a flow meter for metering a desired flow range.

6. The system in accordance with claim 1, wherein the number of flow control valves associated with each column is equal to the number of solvents.

7. The system in accordance with claim 1, wherein each flow control valve maintains a substantially constant flow rate of solvent.

8. The system in accordance with claim 1, further comprising a mixing device associated with each column for mixing the solvent output from at least two of said flow control valves.

9. The system in accordance with claim 1, wherein the system is one of a liquid, gas, fluid, microbore, capillary, preparative, and electro chromatography system.

10. The system in accordance with claim 1, wherein a gradient for each column may be independently specified.

11. The system in accordance with claim 1, wherein a plurality of columns are connected downstream of each flow control valve, said flow control valves controlling the flow rate of the solvent into the respective columns.

12. The system in accordance with claim 1, wherein a plurality of columns are connected upstream of each flow control valve, said flow control valves controlling the flow rate of the solvent from the respective columns.

13. The system in accordance with claim 1, wherein a plurality of columns are connected one of upstream and downstream of each flow control valve, said flow control valves controlling the flow rate of the solvents from the respective columns.

14. The system in accordance with claim 1, wherein the number of flow control valves associated with each lane is equal to a maximum number of different solvents to be mixed to form a gradient in the associated column.

15. The system in accordance with claim 1, further comprising a solvent selection valve disposed in each lane between the pressurized solvent reservoir and the flow control valve.

16. A high throughput high performance chromatography system operating at a high mixing pressure, comprising:
- a plurality of pressurized solvents reservoirs maintaining associated solvents each at substantially constant pressure, the number of solvent reservoirs equaling the number of solvents;
- a plurality of flow control valves connected downstream of each reservoir,
- a plurality of columns connected downstream of the plurality of the valves, each valve controlling the flow rate of one solvent into one column, wherein fluid communication is permitted between each reservoir and a plurality of columns with one valve being disposed within the connection between each reservoir and each column; and
- a plurality of injectors in communication with said plurality of columns such that one injector introduces one sample into one column, the injectors being operable such that multiple samples can be simultaneously introduced into multiple columns and a sample gradient introduced to each column is controllable independent from gradients introduced to other columns.

17. The system in accordance with claim 16, further including a mixing chamber for receiving solvent from at least two reservoirs, the mixing chamber being disposed downstream of the valves associated with at least two reservoirs.

18. The system in accordance with claim 16, wherein the plurality of columns are arranged in parallel.

19. The system in accordance with claim 16, wherein the plurality of valves control the compositional makeup of each solvent that is directed into one column.

20. The system in accordance with claim 16, wherein one column receives a first solvent and another column receives a second solvent that is different from the first solvent.

21. The system in accordance with claim 16, wherein each flow control valve comprises a valve and a flow meter.

22. The system in accordance with claim 16, wherein the number of flow control valves associated with each column is equal to the number of solvents.

23. The system in accordance with claim 16, wherein each flow control valve maintains a substantially constant flow rate of solvent.

* * * * *